US 12,419,354 B2

(12) United States Patent
Hejazi

(10) Patent No.: US 12,419,354 B2
(45) Date of Patent: *Sep. 23, 2025

(54) ATOMIZATION NOZZLE FOR AEROSOL DELIVERY DEVICE

(71) Applicant: RAI Strategic Holdings, Inc., Winston-Salem, NC (US)

(72) Inventor: Vahid Hejazi, Concord, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/242,313

(22) Filed: Sep. 5, 2023

(65) Prior Publication Data

US 2023/0413913 A1    Dec. 28, 2023

Related U.S. Application Data

(63) Continuation of application No. 17/004,572, filed on Aug. 27, 2020, now Pat. No. 11,771,132.

(51) Int. Cl.
*A24F 40/48* (2020.01)
*A24F 40/42* (2020.01)
*A24F 40/50* (2020.01)

(52) U.S. Cl.
CPC .............. *A24F 40/48* (2020.01); *A24F 40/42* (2020.01); *A24F 40/50* (2020.01)

(58) Field of Classification Search
CPC ................ B05B 7/2464; B05B 7/2418; A61M 2205/07; A61M 2205/502; A61M 2205/8206; A61M 11/006; A61M 15/06; A24F 40/10; A24F 40/48; A24F 40/42; A24F 40/50

See application file for complete search history.

(56) References Cited

U.S. PATENT DOCUMENTS

| 4,639,368 A | 1/1987 | Niazi et al. |
| 4,674,519 A | 6/1987 | Kertitsis et al. |
| 4,735,217 A | 4/1988 | Gerth et al. |
| 4,793,365 A | 12/1988 | Sensabaugh et al. |
| 4,807,809 A | 2/1989 | Pryor et al. |

(Continued)

FOREIGN PATENT DOCUMENTS

| JP | 2001507284 A | * 6/2001 |
| WO | WO 1997/06786 | 2/1997 |

(Continued)

OTHER PUBLICATIONS

*Chemical and Biological Studies on New Cigarette Prototypes that Heat Instead of Burn Tobacco*, R. J. Reynolds Tobacco Company Monograph (1988).

(Continued)

*Primary Examiner* — Jean F Duverne
(74) *Attorney, Agent, or Firm* — Womble Bond Dickinson (US) LLP

(57) ABSTRACT

The present disclosure provides aerosol delivery devices having a variety of configurations and arrangements. Some aspects of the disclosure provide aerosol delivery devices having a first pump configured to deliver a flow of air; a second pump configured to deliver a flow of liquid; and a nozzle configured to receive the flow of air and the flow of liquid and output the liquid in an atomized form.

15 Claims, 5 Drawing Sheets

(56) References Cited

U.S. PATENT DOCUMENTS

| | | |
|---|---|---|
| 4,836,224 A | 6/1989 | Lawson et al. |
| 4,889,143 A | 12/1989 | Pryir et al. |
| 4,922,901 A | 5/1990 | Brooks et al. |
| 4,924,887 A | 5/1990 | Raker et al. |
| 4,924,888 A | 5/1990 | Perfetti et al. |
| 4,941,484 A | 7/1990 | Clapp et al. |
| 4,947,874 A | 8/1990 | Brooks et al. |
| 4,972,854 A | 11/1990 | Kiernan et al. |
| 4,987,906 A | 1/1991 | Young et al. |
| 5,025,814 A | 6/1991 | Raker et al. |
| 5,056,537 A | 10/1991 | Brown et al. |
| 5,060,671 A | 10/1991 | Counts et al. |
| 5,093,894 A | 3/1992 | Deevi et al. |
| 5,099,864 A | 3/1992 | Young et al. |
| 5,101,839 A | 4/1992 | Jakob et al. |
| 5,143,097 A | 9/1992 | Sohn et al. |
| 5,154,192 A | 10/1992 | Sprinkel et al. |
| 5,159,942 A | 11/1992 | Brinkley et al. |
| 5,178,878 A | 1/1993 | Wehling et al. |
| 5,220,930 A | 6/1993 | Gentry |
| 5,223,264 A | 6/1993 | Wehling et al. |
| 5,228,460 A | 7/1993 | Sprinkel, Jr. et al. |
| 5,249,586 A | 10/1993 | Morgan et al. |
| 5,261,424 A | 11/1993 | Sprinkel, Jr. et al. |
| 5,322,075 A | 6/1994 | Deevi et al. |
| 5,322,076 A | 6/1994 | Brinkley et al. |
| 5,339,838 A | 8/1994 | Young et al. |
| 5,353,813 A | 10/1994 | Deevi et al. |
| 5,360,023 A | 11/1994 | Blakley et al. |
| 5,372,148 A | 12/1994 | McCafferty et al. |
| 5,377,698 A | 1/1995 | Litzinger et al. |
| 5,468,936 A | 11/1995 | Deevi et al. |
| 5,498,850 A | 3/1996 | Das |
| 5,498,855 A | 3/1996 | Deevi et al. |
| 5,501,237 A | 3/1996 | Young et al. |
| 5,530,225 A | 6/1996 | Hajaligol |
| 5,551,451 A | 9/1996 | Riggs et al. |
| 5,573,692 A | 11/1996 | Das et al. |
| 5,591,368 A | 1/1997 | Fleischhauer et al. |
| 5,665,262 A | 9/1997 | Hajaligol |
| 5,666,977 A | 9/1997 | Higgins et al. |
| 5,697,385 A | 12/1997 | Seymour et al. |
| 5,934,289 A | 8/1999 | Watkins et al. |
| 5,954,979 A | 9/1999 | Counts et al. |
| 5,967,148 A | 10/1999 | Harris et al. |
| 6,040,560 A | 3/2000 | Fleischhauer et al. |
| 6,053,176 A | 4/2000 | Adams et al. |
| 6,102,037 A | 8/2000 | Koch |
| 6,164,287 A | 12/2000 | White |
| 6,196,218 B1 | 3/2001 | Voges |
| 6,216,707 B1 | 4/2001 | Kumar et al. |
| 6,701,936 B2 | 3/2004 | Shafer et al. |
| 6,772,756 B2 | 8/2004 | Shayan |
| 6,803,545 B2 | 10/2004 | Blake et al. |
| 6,810,883 B2 | 11/2004 | Felter et al. |
| 6,854,461 B2 | 2/2005 | Nichols |
| 6,974,590 B2 | 12/2005 | Pather et al. |
| 7,011,096 B2 | 3/2006 | Li et al. |
| 7,017,585 B2 | 3/2006 | Li et al. |
| 7,025,066 B2 | 4/2006 | Lawson et al. |
| 7,040,314 B2 | 5/2006 | Nguyen et al. |
| 7,290,549 B2 | 11/2007 | Banerjee et al. |
| 7,293,565 B2 | 11/2007 | Griffen et al. |
| 7,381,667 B2 | 6/2008 | Bergquist et al. |
| 7,398,783 B2 | 7/2008 | Biggs et al. |
| 7,513,253 B2 | 4/2009 | Kobayashi |
| 7,615,184 B2 | 11/2009 | Lobovsky |
| 7,647,932 B2 | 1/2010 | Cantrell et al. |
| 7,726,320 B2 | 6/2010 | Robinson et al. |
| 7,832,410 B2 | 11/2010 | Hon |
| 7,836,897 B2 | 11/2010 | Borschke et al. |
| 7,896,006 B2 | 3/2011 | Hamano |
| 8,205,622 B2 | 6/2012 | Pan |
| 8,402,976 B2 | 3/2013 | Fernando et al. |
| 8,424,541 B2 | 4/2013 | Crawford et al. |
| 8,430,106 B2 | 4/2013 | Potter et al. |
| 8,627,828 B2 | 1/2014 | Strickland et al. |
| 8,794,231 B2 | 8/2014 | Thorens et al. |
| 8,839,799 B2 | 9/2014 | Conner et al. |
| 8,851,083 B2 | 10/2014 | Oglesby et al. |
| 8,881,737 B2 | 11/2014 | Collett et al. |
| 8,910,639 B2 | 12/2014 | Chang et al. |
| 8,915,254 B2 | 12/2014 | Monsees et al. |
| 9,078,473 B2 | 7/2015 | Worm et al. |
| 9,107,453 B2 | 8/2015 | Dube et al. |
| 9,149,072 B2 | 10/2015 | Conner et al. |
| 9,215,895 B2 | 12/2015 | Bowen et al. |
| 9,220,302 B2 | 12/2015 | DePiano et al. |
| 9,254,002 B2 | 2/2016 | Chong et al. |
| 9,307,787 B2 | 4/2016 | Sun et al. |
| 9,423,152 B2 | 8/2016 | Ampolini et al. |
| 9,484,155 B2 | 11/2016 | Peckerar et al. |
| 9,609,893 B2 | 4/2017 | Novak et al. |
| 9,675,102 B2 | 6/2017 | Hunt et al. |
| 9,861,773 B2 | 1/2018 | Terry et al. |
| 9,974,334 B2 | 5/2018 | Dooley et al. |
| 10,058,123 B2 | 8/2018 | Taluskie et al. |
| 10,058,125 B2 | 8/2018 | Worm et al. |
| 10,172,388 B2 | 1/2019 | Sears et al. |
| 10,196,778 B2 | 2/2019 | Sebastian et al. |
| 10,285,451 B2 | 5/2019 | Bless et al. |
| 10,286,163 B1 | 5/2019 | Paustian et al. |
| 10,500,600 B2 | 12/2019 | Henry, Jr. et al. |
| 10,506,833 B2 | 12/2019 | Manca et al. |
| 10,813,385 B2 | 10/2020 | Sur |
| 10,834,971 B2 | 11/2020 | Manca et al. |
| 11,771,132 B2 * | 10/2023 | Hejazi .................. B05B 7/2418 131/329 |
| 2004/0255968 A1 | 12/2004 | Perfetti et al. |
| 2005/0066986 A1 | 3/2005 | Nestor et al. |
| 2006/0091160 A1 | 5/2006 | Sweeton |
| 2006/0196518 A1 | 9/2006 | Hon |
| 2007/0215167 A1 | 9/2007 | Crooks et al. |
| 2007/0227535 A1 | 10/2007 | Harrington et al. |
| 2008/0236602 A1 | 10/2008 | Bereman |
| 2009/0044818 A1 | 2/2009 | Takeuchi et al. |
| 2009/0241948 A1 | 10/2009 | Clancy et al. |
| 2010/0018539 A1 | 1/2010 | Brinkley et al. |
| 2010/0024834 A1 | 2/2010 | Ogelsby et al. |
| 2010/0307518 A1 | 12/2010 | Wang |
| 2013/0008457 A1 | 1/2013 | Zheng et al. |
| 2013/0255702 A1 | 10/2013 | Griffith et al. |
| 2014/0096781 A1 | 4/2014 | Sears et al. |
| 2015/0020823 A1 | 1/2015 | Lipowicz et al. |
| 2015/0020830 A1 | 1/2015 | Koller et al. |
| 2015/0216232 A1 | 8/2015 | Bless et al. |
| 2015/0313283 A1 | 11/2015 | Collett et al. |
| 2016/0007651 A1 | 1/2016 | Ampolini et al. |
| 2016/0219933 A1 | 8/2016 | Henry, Jr. et al. |
| 2016/0261020 A1 | 9/2016 | Marion et al. |
| 2017/0027220 A1 | 2/2017 | Sebastian et al. |
| 2017/0112196 A1 | 4/2017 | Sur et al. |
| 2017/0280775 A1 | 10/2017 | Manca et al. |
| 2017/0291757 A1 | 10/2017 | Sebastian et al. |
| 2017/0303591 A1 | 10/2017 | Cameron et al. |
| 2018/0020722 A1 | 1/2018 | Davis et al. |
| 2018/0020723 A1 | 1/2018 | Davis et al. |
| 2018/0274354 A1 | 9/2018 | Nesgaard |
| 2018/0279673 A1 | 10/2018 | Sebastian et al. |
| 2019/0082735 A1 | 3/2019 | Phillips et al. |
| 2019/0124979 A1 | 5/2019 | Sebastian et al. |
| 2020/0154871 A1 * | 5/2020 | Novak, III .............. H02J 7/007 |
| 2020/0163389 A1 | 5/2020 | Sur |
| 2021/0128866 A1 | 5/2021 | Higashiyama |
| 2021/0178108 A1 | 6/2021 | Higashiyama |

FOREIGN PATENT DOCUMENTS

| | | |
|---|---|---|
| WO | WO 98/29236 | 7/1998 |
| WO | WO 1998/57556 | 12/1998 |
| WO | WO 2010/003480 | 1/2010 |
| WO | WO 2013/089551 | 6/2013 |
| WO | WO 2013/160129 | 10/2013 |
| WO | WO 2014/182736 | 11/2014 |

(56) References Cited

FOREIGN PATENT DOCUMENTS

| WO | WO 2018/172563 | 9/2018 |
| WO | WO 2020/003305 | 1/2020 |
| WO | WO 2020/089631 | 5/2020 |
| WO | WO 2020/089633 | 5/2020 |
| WO | WO 2020/089634 | 5/2020 |
| WO | WO 2020/089635 | 5/2020 |
| WO | WO 2020/089636 | 5/2020 |
| WO | WO 2020/089637 | 5/2020 |
| WO | WO 2020/089638 | 5/2020 |
| WO | WO 2020/089639 | 5/2020 |
| WO | WO 2020/089640 | 5/2020 |
| WO | WO 2020/089641 | 5/2020 |

OTHER PUBLICATIONS

Leffingwell et al., "Tobacco Flavoring for Smoking Products", *R. J. Reynolds Tobacco Company*, 1972, pp. 1-72.

\* cited by examiner

ATOMIZATION NOZZLE FOR AEROSOL DELIVERY DEVICE

CROSS-REFERENCE TO RELATED APPLICATIONS

This application is a continuation of U.S. application Ser. No. 17/004,572 filed on Aug. 27, 2020, which is incorporated herein by reference in its entirety.

BACKGROUND

Field of the Disclosure

The present disclosure relates to aerosol delivery devices, and more particularly to an aerosol delivery device which may utilize electrical power to atomize an aerosol precursor composition for the production of an aerosol. In various embodiments, the aerosol precursor composition, which may incorporate materials and/or components that may be made or derived from tobacco or otherwise incorporate tobacco or other plants, may include natural or synthetic components including flavorants, and/or may include one or more medicinal components, is atomized to produce an inhalable substance for human consumption.

Description of Related Art

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices, and heat generating sources set forth in the background art described in U.S. Pat. No. 7,726,320 to Robinson et al., U.S. Pat. App. Pub. No. 2013/0255702 to Griffith Jr. et al., and U.S. Pat. App. Pub. No. 2014/0096781 to Sears et al., which are incorporated herein by reference in their entireties. See also, for example, the various types of smoking articles, aerosol delivery devices, and electrically powered sources referenced by brand name and commercial source in U.S. Pat. App. Pub. No. 2015/0216232 to Bless et al., which is incorporated herein by reference in its entirety. However, it would be desirable to provide an aerosol delivery device with enhanced functionality. In this regard, it is desirable to provide an aerosol delivery with advantageous features.

BRIEF SUMMARY

The present disclosure relates to aerosol delivery devices, methods of forming such devices, and elements of such devices. In some embodiments of the present disclosure, an aerosol delivery device, may comprise a first pump configured to deliver a flow of air; a second pump configured to deliver a flow of liquid; and a nozzle configured to receive the flow of air and the flow of liquid and output the liquid in an atomized form. In some embodiments, the first pump may be selected from the group consisting of a micro-compressor pump, a micro-blower, a rotary micro-pump, a diaphragm micro-pump, and a piezoceramic micro-pump. In some embodiments, the first pump may be configured to deliver the flow of air to the nozzle at a flow rate in the range of about 1 L/min to about 10 L/min and a pressure in the range of about 0.1 psi to about 10 psi. In some embodiments, the first pump may further comprise a filter component configured to reduce accumulation of particulates in the first pump.

In some embodiments, the second pump may be selected from the group consisting of a centrifugal micro-pump, a ring micro-pump, a rotary micro-pump, a diaphragm micro-pump, a peristaltic micro-pump, and a step micro-pump. In some embodiments, the second pump may be configured to deliver the flow of liquid to the nozzle at a flow rate in the range of about 0.1 mL/min to about 10 mL/min and a pressure in the range of about 0.1 psi to about 10 psi. In some embodiments, the nozzle may comprise an orifice adapted to spray the atomized liquid. In some embodiments, the pressurized flow of air and the pressurized flow of liquid are mixed within the nozzle prior to being transferred to the orifice. In some embodiments, the pressurized flow of air and the pressurized flow of the liquid composition are separately transferred to the orifice without mixing within the nozzle. In some embodiments, the aerosol delivery device may have a fluid pressure within the nozzle in the range of about 0.1 psi to about 10 psi.

In some embodiments, the nozzle may be positioned proximate to a mouthpiece portion. In some embodiments, the mouthpiece portion may be configured to receive a flow of the atomized liquid from the nozzle and has an opening for egress of the atomized liquid from the mouthpiece portion. In some embodiments, the aerosol delivery device may further comprise a reservoir configured to contain a liquid composition and in fluid communication with the second pump. In some embodiments, the reservoir may be removable or replaceable. In some embodiments, the reservoir may be permanently positioned within the aerosol delivery device and is configured to be refillable by a user of the device. In some embodiments, the liquid composition may be an aerosol precursor composition. In some embodiments, the aerosol precursor composition may comprise one or more of a polyhydric alcohol, nicotine, tobacco, a tobacco extract, or a flavorant. In some embodiments, the aerosol precursor composition may additionally or alternatively include other active ingredients including, but not limited to, a nicotine component, botanical ingredients (e.g., lavender, peppermint, chamomile, basil, rosemary, ginger, *cannabis*, *ginseng*, maca, hemp, *eucalyptus*, rooibos, fennel, citrus, cloves, and tisanes), stimulants (e.g., caffeine and guarana), amino acids (e.g., taurine, theanine, phenylalanine, tyrosine, and tryptophan) and/or pharmaceutical, nutraceutical, medicinal ingredients (e.g., vitamins, such as B6, B12, and C, and/or cannabinoids, such as tetrahydrocannabinol (THC) and cannabidiol (CBD)). In some embodiments, the aerosol precursor composition may comprise about 60% or greater water by weight, based on the total weight of the water-based aerosol precursor composition.

In some embodiments, the aerosol delivery device may further comprise a power source and a control component. In some embodiments, the control component may be configured to control an output flow rate of the first pump and/or an output flow rate of the second pump. In some embodiments, the control component may be configured to control power output from the power source to the first pump and/or the second pump. In some embodiments, the power source may be configured to provide sufficient power to operate both the first pump and the second pump simultaneously. In some embodiments, the control component may be configured to control the function of any component within the aerosol delivery device, independently, or in combination with one or more other components therein.

In some embodiments, the aerosol delivery device may further comprise a housing. In some embodiments, the first pump, the second pump, and the nozzle may be positioned within the housing. In some embodiments, the aerosol delivery device may further comprise at least one opening in the housing for receiving air. In some embodiments, the first pump may be in fluid communication with the at least one opening such that air is drawn into the first pump from outside of the aerosol delivery device when the first pump is activated. In some embodiments, the housing may be a first body with a replaceable cartridge comprising at least a reservoir. In some embodiments, the housing may be a control body and the first pump, the second pump, and the nozzle may be positioned within a replaceable cartridge. In some embodiments, the first pump, the second pump, and the nozzle may be provided in a reusable component and the reservoir may be removable, replaceable, and/or refillable. For example, the housing may be a control body; the first pump, the second pump, and the nozzle may be provided in a reusable atomizing section; and the reservoir may be provided in a replaceable and/or reusable reservoir section. In other embodiments, the housing may be a control body including the first pump, the second pump, the nozzle, and the reservoir, wherein the reservoir is configured to be refillable by a user of the device. Generally, the aerosol delivery device may have a one-piece design (e.g., forming a singular body including all components of the device), a two-piece design (e.g., having two detachable sections), a three-piece design (e.g., having three detachable sections), or more, wherein each detachable section may be either reusable or replaceable.

The invention includes, without limitation, the following embodiments.

Embodiment 1: An aerosol delivery device, comprising: a first pump configured to deliver a flow of air; a second pump configured to deliver a flow of liquid; and a nozzle configured to receive the flow of air and the flow of liquid and output the liquid in an atomized form.

Embodiment 2: An aerosol delivery device of any preceding embodiment, wherein the first pump is selected from the group consisting of a micro-compressor pump, a micro-blower, a rotary micro-pump, a diaphragm micro-pump, and a piezoceramic micro-pump.

Embodiment 3: An aerosol delivery device of any preceding embodiment, wherein the first pump is configured to deliver the flow of air to the nozzle at a flow rate in the range of about 1 L/min to about 10 L/min and a pressure in the range of about 0.1 psi to about 10 psi.

Embodiment 4: An aerosol delivery device of any preceding embodiment, wherein the first pump further comprises a filter component configured to reduce accumulation of particulates in the first pump.

Embodiment 5: An aerosol delivery device of any preceding embodiment, wherein the second pump is selected from the group consisting of a centrifugal micro-pump, a ring micro-pump, a rotary micro-pump, a diaphragm micro-pump, a peristaltic micro-pump, and a step micro-pump.

Embodiment 6: An aerosol delivery device of any preceding embodiment, wherein the second pump is configured to deliver the flow of liquid to the nozzle at a flow rate in the range of about 0.1 mL/min to about 10 mL/min and a pressure in the range of about 0.1 psi to about 10 psi.

Embodiment 7: An aerosol delivery device of any preceding embodiment, wherein the nozzle comprises an orifice adapted to spray the atomized liquid.

Embodiment 8: An aerosol delivery device of any preceding embodiment, wherein the pressurized flow of air and the pressurized flow of liquid are mixed within the nozzle prior to being transferred to the orifice.

Embodiment 9: An aerosol delivery device of any preceding embodiment, wherein the pressurized flow of air and the pressurized flow of the liquid composition are separately transferred to the orifice without mixing within the nozzle.

Embodiment 10: An aerosol delivery device of any preceding embodiment, wherein the fluid pressure within the nozzle is in the range of about 0.1 psi to about 10 psi.

Embodiment 11: An aerosol delivery device of any preceding embodiment, wherein the nozzle is positioned proximate to a mouthpiece portion.

Embodiment 12: An aerosol delivery device of any preceding embodiment, wherein the mouthpiece portion is configured to receive a flow of the atomized liquid from the nozzle and has an opening for egress of the atomized liquid from the mouthpiece portion.

Embodiment 13: An aerosol delivery device of any preceding embodiment, further comprising a reservoir configured to contain a liquid composition and in fluid communication with the second pump.

Embodiment 14: An aerosol delivery device of any preceding embodiment, wherein the reservoir is removable and replaceable by a user of the aerosol delivery device.

Embodiment 15: An aerosol delivery device of any preceding embodiment, wherein the reservoir is refillable by a user of the aerosol delivery device.

Embodiment 16: An aerosol delivery device of any preceding embodiment, wherein the liquid composition is an aerosol precursor composition.

Embodiment 17: An aerosol delivery device of any preceding embodiment, wherein the aerosol precursor composition comprises one or more of a polyhydric alcohol, nicotine, tobacco, a tobacco extract, a flavorant, and other active ingredients including, but not limited to, a nicotine component, botanical ingredients (e.g., lavender, peppermint, chamomile, basil, rosemary, ginger, *cannabis*, *ginseng*, maca, hemp, *eucalyptus*, rooibos, fennel, citrus, cloves, and tisanes), stimulants (e.g., caffeine and guarana), amino acids (e.g., taurine, theanine, phenylalanine, tyrosine, and tryptophan) and/or pharmaceutical, nutraceutical, medicinal ingredients (e.g., vitamins, such as B6, B12, and C, and/or cannabinoids, such as tetrahydrocannabinol (THC) and cannabidiol (CBD)), and combinations thereof.

Embodiment 18: An aerosol delivery device of any preceding embodiment, wherein the aerosol precursor composition is water-based so as to comprise about 60% or greater water by weight, based on the total weight of the aerosol precursor composition.

Embodiment 19: An aerosol delivery device of any preceding embodiment, further comprising a power source and a control component.

Embodiment 20: An aerosol delivery device of any preceding embodiment, wherein the control component is configured to control an output flow rate of one or both of the first pump and the second pump.

Embodiment 21: An aerosol delivery device of any preceding embodiment, wherein the control component is configured to control the power output from the power source to one or both of the first pump and the second pump.

Embodiment 22: An aerosol delivery device of any preceding embodiment, wherein the power source is configured to provide sufficient power to operate both the first pump and the second pump simultaneously.

Embodiment 23: An aerosol delivery device of any preceding embodiment, further comprising a housing.

Embodiment 24: An aerosol delivery device of any preceding embodiment, wherein the first pump, the second pump, and the nozzle are positioned within the housing.

Embodiment 25: An aerosol delivery device of any preceding embodiment, further comprising at least one opening in the housing for receiving air.

Embodiment 26: An aerosol delivery device of any preceding embodiment, wherein the first pump is in fluid communication with the at least one opening such that air is drawn into the first pump from outside of the aerosol delivery device when the first pump is activated.

Embodiment 27: An aerosol delivery device of any preceding embodiment, wherein the housing is a first body with a replaceable cartridge comprising at least a reservoir.

Embodiment 28: An aerosol delivery device of any preceding embodiment, wherein the housing is a control body and the first pump, the second pump, and the nozzle are positioned within a replaceable cartridge.

Embodiment 29: An aerosol deliver device of any preceding embodiment, wherein the housing is a control body; the first pump, the second pump, and the nozzle are positioned in a reusable atomizing section; and the reservoir is positioned in a replaceable reservoir section.

Embodiment 30: An aerosol delivery device of any preceding embodiment, wherein the housing is a control body including the first pump, the second pump, the nozzle, and the reservoir, wherein the reservoir is configured to be one or more of removable, replaceable, and refillable by a user of the device.

Embodiment 31: An aerosol delivery device of any preceding embodiment, further comprising a control body, a reservoir section having a reservoir positioned therein, and an atomizing section having the first pump, the second pump, and the nozzle positioned therein.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a particular embodiment description herein. This disclosure is intended to be read holistically such that any separable features or elements of the disclosed invention, in any of its various aspects or embodiments, should be viewed as combinable unless the context clearly dictates otherwise.

BRIEF DESCRIPTION OF THE DRAWING(S)

In order to assist the understanding of aspects of the disclosure, reference will now be made to the appended drawings, which are not necessarily drawn to scale and in which like reference numerals refer to like elements. The drawings are provided by way of example to assist understanding of aspects of the disclosure, and should not be construed as limiting the disclosure.

FIG. 1 illustrates a component view of a portion of an example aerosol delivery device including a first pump, a second pump, a nozzle, and a reservoir, according to an example embodiment of the present disclosure;

FIG. 2 illustrates a front cross-section schematic view of an example aerosol delivery device having a one-piece design including a reservoir, a first pump, a second pump, and a nozzle, according to an example embodiment of the present disclosure; and FIG. 3 illustrates a front cross-section schematic view of an example aerosol delivery device having a two-piece design including a cartridge and a control body, wherein the cartridge and control body are shown in a de-coupled configuration, according to an example embodiment of the present disclosure;

DETAILED DESCRIPTION

Figure 1:
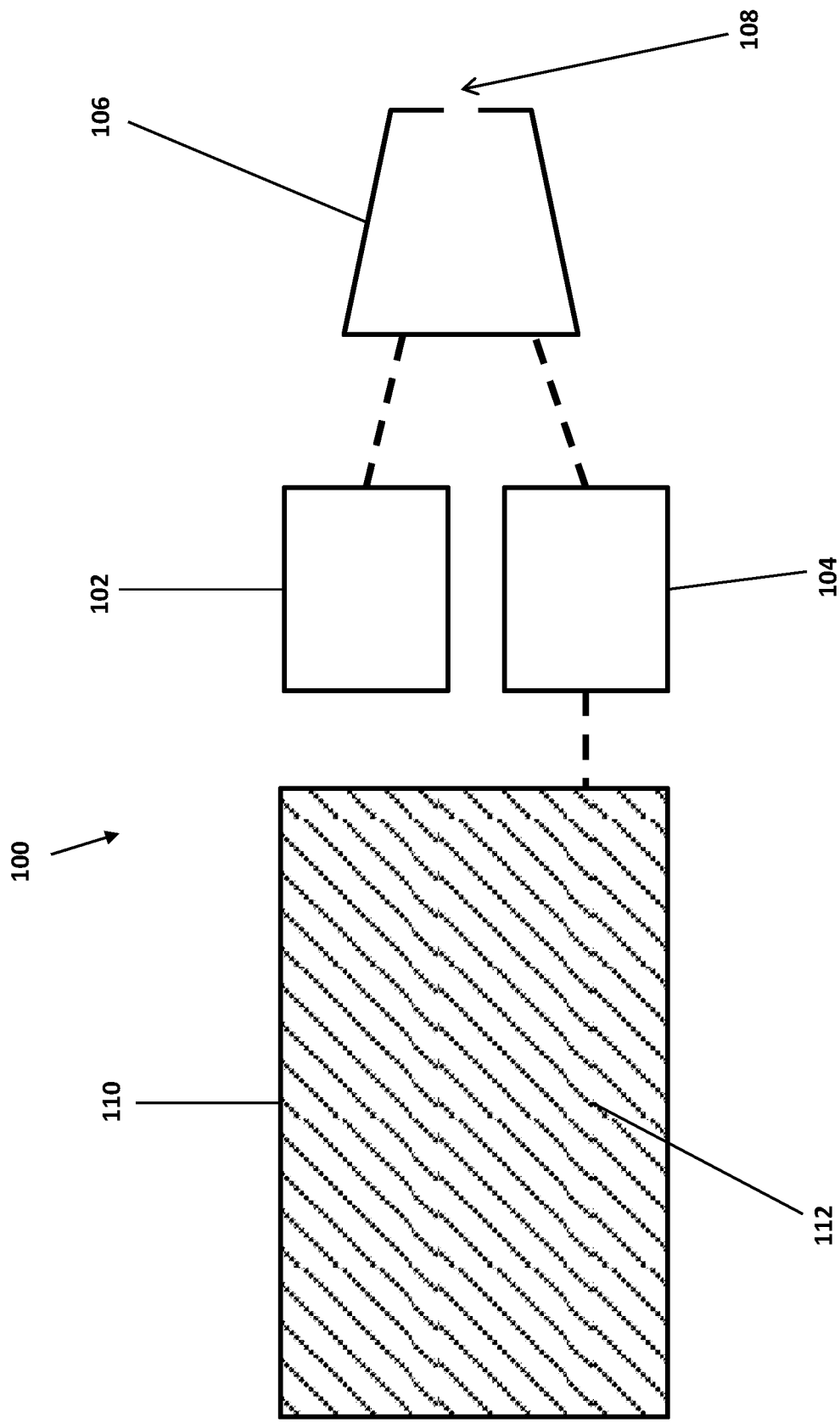

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification and the appended claims, the singular forms "a," "an," "the" and the like include plural referents unless the context clearly dictates otherwise. Also, while reference may be made herein to quantitative measures, values, geometric relationships or the like, unless otherwise stated, any one or more if not all of these may be absolute or approximate to account for acceptable variations that may occur, such as those due to engineering tolerances or the like. As used herein, "substantially free" refers to concentrations of a given substance of less than 1% by weight or less than 0.5% by weight or less than 0.1% by weight based on total weight of a material.

As described hereinafter, embodiments of the present disclosure relate to aerosol delivery devices or vaporization devices, said terms being used herein interchangeably. Aerosol delivery devices according to the present disclosure use electrical energy to vaporize a material (preferably without combusting the material to any significant degree and/or without significant chemical alteration of the material) to form an inhalable substance; and components of such devices have the form of articles that most preferably are sufficiently compact to be considered hand-held devices. That is, use of components of some aerosol delivery devices does not result in the production of smoke—i.e., from by-products of combustion or pyrolysis of tobacco, but rather, use of those preferred systems results in the production of vapors resulting from vaporization of an aerosol precursor composition. In some examples, components of aerosol delivery devices may be characterized as electronic cigarettes, and those electronic cigarettes most preferably incorporate tobacco and/or components derived from tobacco, and hence deliver tobacco derived components in aerosol form. Other examples include delivery devices for cannabinoids, such as Tetrahydrocannabinol (THC) and/or Cannabidiol (CBD), botanicals, medicinals, nutraceuticals, and/or other active ingredients.

Aerosol generating devices of certain preferred aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating device of the present disclosure can hold and use the device much like a smoker employs a traditional type of smoking article, draw on one end of that device for inhalation of aerosol produced by that device, take or draw puffs at selected intervals of time, and the like.

Aerosol delivery devices of the present disclosure also may be characterized as being vapor-producing articles or medicament delivery articles. Thus, such articles or devices may be adapted so as to provide one or more substances (e.g., flavors and/or pharmaceutical active ingredients) in an inhalable form or state. For example, inhalable substances may be substantially in the form of a vapor (i.e., a substance that is in the gas phase at a temperature lower than its critical point). Alternatively, inhalable substances may be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., processing circuitry, such as may comprise a microcontroller or microprocessor), an atomization assembly (e.g., means for aerosolizing a liquid composition, such as may comprise one or more pumps, optionally configured to provide varying flow characteristics, and an atomization nozzle), a reservoir configured to contain a liquid composition (e.g., commonly an aerosol precursor composition liquid capable of yielding an aerosol, such as ingredients commonly referred to as "smoke juice," "e-liquid" and "e-juice"), and a mouthpiece or mouth region for allowing draw upon the aerosol delivery device for aerosol inhalation (e.g., a defined airflow path through the article such that aerosol generated may be withdrawn therefrom upon draw).

Alignment of the components within the aerosol delivery device and/or the configuration of the device overall may be variable. For example, the aerosol delivery device may have a one-piece design (e.g., forming a singular body including all components of the device), a two-piece design (e.g., having two detachable sections), a three-piece design (e.g., having three detachable sections), or more. Typically, the components within each individual section and/or the arrangement of those components within each individual section may vary. In some embodiments, for example, various sections of the device and/or components within those sections may be considered to removable, replaceable, or reusable. In specific embodiments, the aerosol precursor composition may be located between two opposing ends of the device (e.g., within a reservoir of a cartridge, which in certain circumstances is replaceable, disposable, reusable, and/or refillable). Other configurations, however, are not excluded. Generally, the components are configured relative to one another so that energy from the atomization assembly vaporizes the aerosol precursor composition (as well as one or more flavorants, medicaments, or the like that may likewise be provided for delivery to a user) and forms an aerosol for delivery to the user. When the atomization assembly vaporizes the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof.

More specific formats, configurations and arrangements of components within the aerosol delivery devices of the present disclosure will be evident in light of the further disclosure provided hereinafter. Additionally, the selection and arrangement of various aerosol delivery device components may be appreciated upon consideration of the commercially available electronic aerosol delivery devices, such as those representative products referenced in the background art section of the present disclosure.

FIG. 1 illustrates a component view of various components that may be provided in an aerosol delivery device according to the present disclosure. For example, the aerosol delivery device 100 may comprise a first pump 102 configured to deliver a flow of air at a first flow rate and pressurized at a first pressure range, a second pump 104 configured to deliver a flow of liquid at a second flow rate and pressurized at a second pressure range, and a nozzle 106 configured to receive the flow of air and the flow of liquid and output the liquid in an atomized form. In some embodiments, the nozzle may further comprise an orifice 108 adapted to spray the atomized liquid. As depicted in FIG. 1, the aerosol delivery device may further comprise a reservoir 110 configured to contain a liquid composition 112 and in fluid communication with the second pump 104. In some embodiments, the first pump, the second pump, the nozzle, and/or the reservoir may be interconnected either directly or indirectly to provide fluid communication between the various components, for example, as illustrated by the dashed lines in FIG. 1. Therefore, the dashed lines are intended to represent interconnection of various components which may (e.g., for indirect connection) or may not (e.g., for direct connection) require one or more additional components in order to facilitate the connection of various components.

Figure 2:
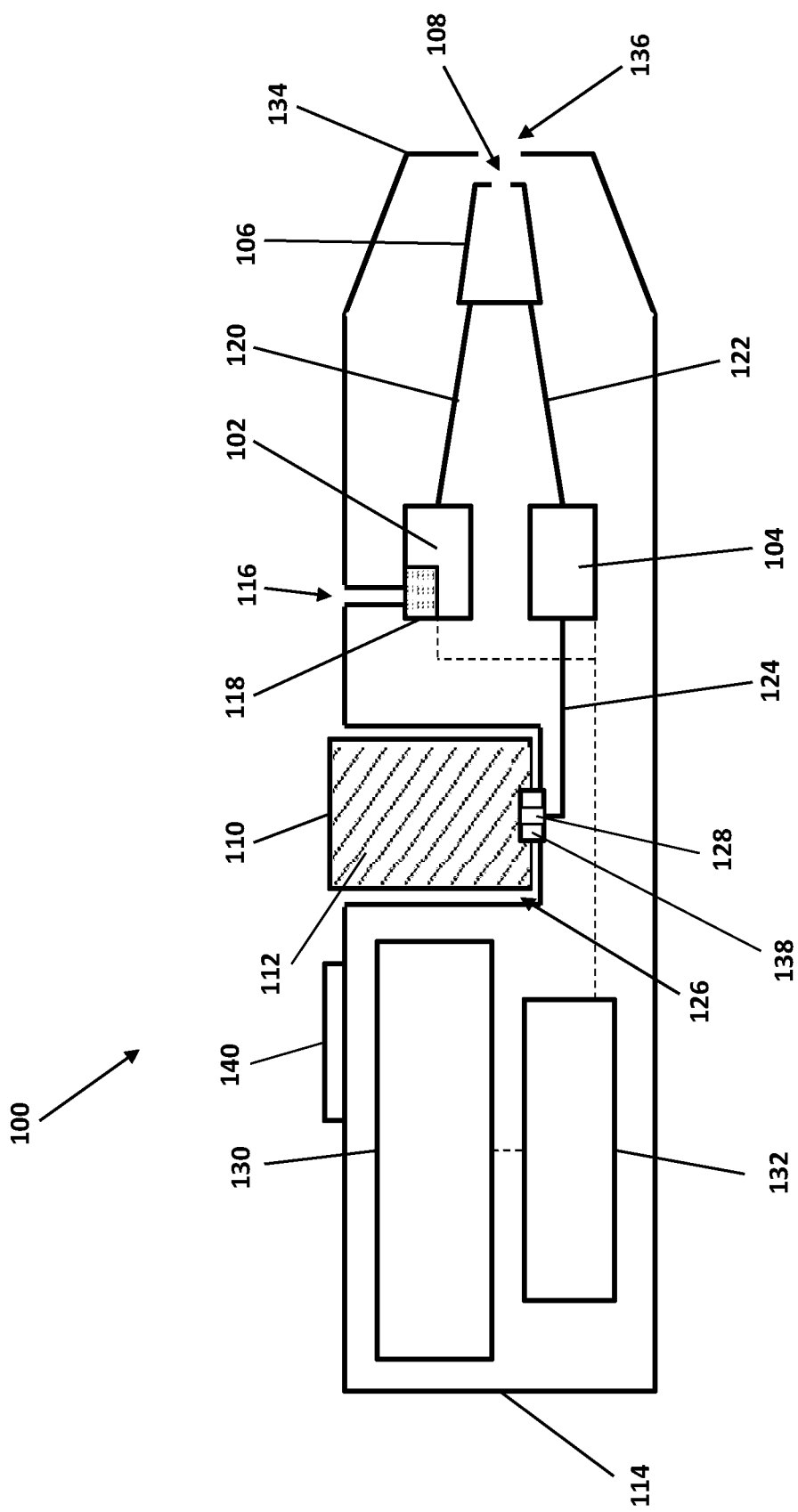

FIG. 2 illustrates an aerosol delivery device having a one-piece design including a reservoir, a first pump, a second pump, and a nozzle, according to one embodiment of the present disclosure. In the depicted embodiment, various components of the aerosol delivery device may be provided within an outer housing 114. For example, a first pump 102, a second pump 104, a nozzle 106 comprising an orifice 108, and a reservoir 110 configured to contain a liquid composition 112 may all be included within the housing 114 of the aerosol delivery device.

In the depicted embodiment, the first pump 102 may be configured to deliver a flow of air at a first flow rate and pressurized at a first pressure range. In some embodiments, the first pump may be in the form of an air pump or a micro-blower configured to transfer the pressurized air to the nozzle 106. In some embodiments, the first pump 102 may be configured to deliver air to the nozzle 106 at a flow rate in the range of about 0.1 L/min to about 20 L/min, about 1 L/min to about 10 L/min, or about 3 L/min to about 6 L/min. In some embodiments, the first pump may be configured to deliver air to the nozzle at a flow rate of at least about 1 L/min, at least about 5 L/min, at least about 10 L/min, at least about 15 L/min, or at least about 20 L/min. In some embodiments, the first pump is configured to deliver air to the nozzle at a pressure in the range of about 0.1 psi to about 10 psi, about 0.5 psi to about 5 psi, or about 1 psi to about 2.5 psi. In some embodiments, the first pump may be configured to deliver air to the nozzle at a pressure of at least about 0.1 psi, at least about 0.5 psi, at least about 1 psi, at least about 2.5 psi, at least about 5 psi, at least about 7.5 psi, or at least about 10 psi. It should be noted that all pressure values referred to herein are intended to define a relative pressure output (e.g., the pressure relative to ambient pressure) rather than absolute pressure.

Suitable air pumps may include, but are not limited to, a micro-compressor pump, a micro-blower, a rotary micro-pump, a diaphragm micro-pump, and a piezoceramic micro-pump. In some embodiments, such as the embodiment depicted in FIG. 2, the aerosol delivery device may further comprise at least one opening 116 for receiving air. In some embodiments, the first pump 102 is in fluid communication with the at least one opening 116 such that air is drawn into the first pump 102 from outside of the aerosol delivery device when the first pump 102 is activated. Although the at least one opening 116 is illustrated as a separate element, it is understood that additionally, or alternatively, the at least one opening may coincide with a further opening already present in the device. For example, as discussed below, the device includes a cavity 126 for receiving the reservoir 110, and the at least one opening may comprise a channel or the like extending through the device and opening into the cavity 116. Further, the aerosol delivery device may include a generally open interior space, and sufficient air intake may be available to the first pump 102 through the cavity 126 opening into the generally open interior space. In some embodiments, the first pump 102 may further comprise a filter component 118 configured to reduce the amount of particulates that accumulate inside the first pump. In some embodiments, the first pump may be connected to the nozzle via a conduit 120 capable of transferring the pressurized flow of air from the first pump 102 to the nozzle 106. In some embodiments, the conduit may be in the form of a hollow tubing or casing capable of transporting a pressurized flow of air, for example. Various types of tubing or conduits may be suitable for use in aerosol delivery devices according to the present disclosure.

As noted above, the second pump 104 may be configured to deliver a flow of liquid at a second flow rate and pressurized at a second pressure range. In some embodiments, the second pump 104 may be in the form of a pressurized liquid pump. For example, the second pump may be configured to deliver the liquid composition to the nozzle at a flow rate in the range of about 0.1 mL/min to about 10 mL/min, or about 0.2 to about 5 mL/min, or about 0.5 to about 2 mL/min. In some embodiments, the second pump may be configured to deliver the liquid composition to the nozzle at a flow rate of about 10 mL/min or less, about 7.5 mL/min or less, about 5 mL/min or less, about 2.5 mL/min or less, or about 1 mL/min or less. In some embodiments, the liquid pump is configured to deliver the liquid composition at a pressure in the range of about 0.1 psi to about 10 psi, about 0.5 psi to about 5 psi, or about 1 psi to about 2.5 psi. in some embodiments, the liquid pump is configured to deliver the liquid composition at a pressure of about of about 10 psi or less, about 7.5 psi or less, about 5 psi or less, about 2.5 psi or less, or about 1 psi or less. Suitable liquid pumps may include, but are not limited to, a centrifugal micro-pump, a ring micro-pump, a rotary micro-pump, a diaphragm micro-pump, a peristaltic micro-pump, and a step micro-pump. In some embodiments, the second pump may be connected to the nozzle via a first liquid transport element 122 capable of transferring the pressurized flow of air from the first pump 102 to the nozzle 106. In some embodiments, the first liquid transport element may be in the form of a hollow tubing or casing capable of transporting a pressurized flow of liquid, for example. Various types of tubing and/or liquid transport elements may be suitable for use in aerosol delivery devices according to the present disclosure.

In some embodiments, the second pump 104 may be in fluid communication with the reservoir 110 and configured to transfer a flow of the liquid composition 112 from the reservoir 110 to the nozzle 106. In various embodiments, the reservoir 110 may be in fluid communication with (either directly or through one or more additional components, as noted above with respect to FIG. 1) the second pump. For example, in the depicted embodiment of FIG. 2, the reservoir 110 is in fluid communication with the second pump 104 via a second liquid transport element 124. The second liquid transport element 124 can transport the liquid composition 112 stored in the reservoir 110 to the second pump 104, thus providing fluid communication between the second pump 104 and the reservoir 110. In such a manner, the second liquid transport element enables fluid transport between the reservoir 110 and the nozzle 106, e.g., such that the liquid composition may be conveyed from the reservoir to the nozzle. In some embodiments, the second liquid transport element may be in the form of a hollow tubing or casing capable of transporting a flow of the liquid composition at the required pressure conditions.

Various types of reservoirs may also be suitable for use in embodiments of the present disclosure. In some embodiments, for example, the liquid reservoir may comprise an independent container (e.g., formed of walls substantially impermeable to the liquid composition), which, in some embodiments, may be configured to be removed, replaced, and/or refilled by a user of the device. In some embodiments, the reservoir may define a substantially self-contained portion or section of the aerosol delivery device, or the reservoir may be provided as a component within the housing of the aerosol delivery device or a portion of the aerosol delivery device (e.g., a control unit, and atomizing section, or a cartridge portion) as discussed further herein. For example, as noted above, the aerosol delivery device may have a one-piece design (e.g., including the reservoir within the housing of the device, or the reservoir being removably attachable to the one-piece device), a two-piece design (e.g., including a control unit and a cartridge portion, wherein the reservoir may be included as a component within either), or a three-piece design (e.g., including a control unit, an atomizing section, and a reservoir housing, e.g., where the reservoir is self-contained within the reservoir housing). It should be noted that the configuration of the reservoir is not intended to be limiting and generally the reservoir may be removed, replaced, and/or refilled by a user of the device irrespective of the configuration of the overall device.

As depicted in FIG. 2, in some embodiments there may be a cavity 126 defined within the housing 114 of the aerosol delivery device to facilitate removal of the liquid reservoir 110 (e.g., to facilitate replacement of the liquid reservoir or refilling and reuse of the existing liquid reservoir. In such embodiments, the cavity may further comprise a locking interface 128 which is configured to lock the reservoir 110 in place when inserted into the cavity 126 by a user of the aerosol delivery device. The locking interface may be configured to puncture the bottom of the reservoir in a sealed arrangement such that the liquid contained therein can be released to the second liquid transport element 124 or, in some embodiments, directly to the second pump 104. Such configurations and locking interfaces may vary and any mechanism suitable for securing the reservoir in place and providing transfer of the liquid composition therefrom may be suitable. In some embodiments, the walls of the liquid reservoir may be flexible and/or collapsible, while in other embodiments the walls of the liquid reservoir may be substantially rigid. In some embodiments, the liquid reservoir may be substantially sealed to prevent passage of the liquid composition therefrom except via any specific openings or conduits provided expressly for passage of the liquid composition, such as through one or more transport elements as otherwise described herein. For example, the reservoir 110 may include a sealing member 138 configured to form a seal around the locking interface 128 to prevent or significantly reduce leaking of the liquid composition 112 from the reservoir after contact with the locking interface. If desired, further embodiments for securing the reservoir 110 into the cavity 126 are also encompassed. For example, the reservoir 110 and the cavity 126 may have matching screw threads, matching magnetic elements, or the like. In other embodiments, the reservoir 110 may be contained entirely within the housing 114 of an aerosol delivery device having a one-piece design (not pictured. In such embodiments, the reservoir may be configured such that it is refillable by a user of the aerosol delivery device without being physically removed from the housing.

Other example embodiments of reservoirs and transport elements useful in aerosol delivery devices according to the present disclosure may vary, and such reservoirs and/or transport elements can be incorporated into devices such as those described herein. In some embodiments, a microfluidic chip may be embedded in the reservoir 110, and the amount and/or mass of liquid composition delivered from the reservoir may be controlled by the second pump, such as one based on microelectromechanical systems (MEMS) technology. In some embodiments, the second pump may be directly connected to the reservoir and/or the nozzle, for example, such that liquid is pumped directly from the reservoir via the second pump to the nozzle, whereby use of one or more transport elements is not necessary. In some embodiments, the second pump may optionally be positioned within the reservoir such that the second pump and the reservoir form a single component within the cartridge. Examples of suitable micropumps for use in embodiments of the present disclosure can be found, for example in U.S. patent application Ser. No. 16/203,069, directed to Micropump for an Aerosol Delivery Device, filed on Nov. 28, 2018; as well as U.S. Pat. No. 10,285,451 to Bless, both of which are incorporated herein by reference in their entireties.

As noted above, the nozzle 106 may be positioned within the housing 114 of the aerosol delivery device and configured to receive the flow of air (from the first pump 102) and the flow of liquid (from the second pump 104) and output the liquid in an atomized form. In the depicted embodiment of FIG. 2, the nozzle 106 is in fluid communication with a pressurized flow of air delivered from the first pump 102 and a pressurized flow of the liquid composition from the second pump 104. As noted above, in accordance with some embodiments, the pressurized flow of air is delivered from the first pump 102 to the nozzle 106 via a conduit 120, such that the nozzle is in fluid communication with the air pump 102; and the pressurized flow of the liquid composition is delivered from the second pump 104 to the nozzle 106 via a first liquid transport element 122. In other embodiments, delivery of the pressurized flow of air and/or the pressurized flow of liquid to the nozzle 106 may occur on demand, such as, for example, via control from a control component 132 which will be discussed further herein below. In some embodiments, nozzles as described herein may provide for mixing of the liquid composition and air either internally or externally. For example, internal mixing nozzles allow the pressurized flow of air and the pressurized flow of the liquid composition to be mixed internally (within the nozzle) prior to being transferred to the orifice. On the other hand, external mixing nozzles allow the pressurized flow of air and the pressurized flow of the liquid composition to be separately transferred to the orifice without mixing within the nozzle. In some embodiments the nozzle may comprise a single orifice 108 that is adapted to spray a singular flow of atomized liquid formed from a mixture of the pressurized flow of air and the pressurized flow of the liquid composition, as depicted in FIG. 2 (e.g., using an internal mixing nozzle) or, in other embodiments, the orifice 108 may comprise a plurality of smaller orifices designed to spray the pressurized flow of air and the pressurized flow of liquid separately (e.g., using an external mixing nozzle). In the latter configuration, for example, the nozzle may contain a center orifice designed to spray the liquid composition, the center orifice being surrounded by a plurality of angular orifices designed to spray multiple pressurized flows of air directly in the path of the flow of the liquid composition, thus forming an aerosol. The types, sizes, and configurations of nozzles and the orifices provided therein may vary. Suitable nozzle assemblies may include, for example, but are not limited to, atomizing nozzles, vaporizing nozzles, external mixing nozzles, internal mixing nozzles, and any type of nozzle suitable for atomizing a liquid composition with a flow of air. Examples of atomizing nozzles are described in U.S. Pat. App. Pub. No. 2018/0289076 to Manca et al. and U.S. Pat. App. Pub. No. 2019/0045847 to Manca et al., both of which are incorporated herein by reference in their entirety. Generally, the fluid pressure within the nozzle, or immediately exiting the nozzle, will be substantially the same as the pressurized flow of air. For example, in some embodiments, the fluid pressure within the nozzle, or immediately upon exiting the nozzle, may be in the range of about 0.1 psi to about 10 psi, about 0.5 psi to about 5 psi, or about 1 psi to about 2.5 psi. In some embodiments, the fluid pressure within the nozzle may be about 10 psi or less, about 7.5 psi or less, about 5 psi or less, about 2.5 psi or less, or about 1 psi or less.

In further embodiments, the aerosol delivery device 100 may comprise a power source 130 and a control component 132. In some embodiments, the power source may be configured to provide sufficient power to operate both the first and second pumps and the control component at the same time. In some embodiments, for example, the power source may be configured to provide sufficient power to operate both the first pump and the second pump simultaneously while providing sufficient power to one or more flow controlling components configured to control the output flow rate from the first and second pumps. Examples of useful power sources include lithium-ion batteries that may be rechargeable, e.g., a rechargeable lithium-manganese dioxide battery. In particular, lithium polymer batteries can be used as such batteries can provide increased safety. Other types of batteries, e.g., N50-AAA CADNICA nickel-cadmium cells, may also be used. In some embodiments, the power source may comprise low wattage lithium-ion batteries, for example, having an energy capacity generally in the range of about 500 mAh to about 3000 mAh and a voltage in the range of about 3 V to about 5 V. Additionally, a power source may be sufficiently lightweight to not detract from a desirable smoking experience. Some examples of possible power supplies are described in U.S. Pat. No. 9,484,155 to Peckerar et al. and U.S. Patent Application Publication No. 2017/0112191 to Sur et al., filed Oct. 21, 2015, the disclosures of which are incorporated herein by reference in their respective entireties.

In some embodiments, the power source, for example, may include a replaceable battery or a rechargeable battery, lithium-ion battery, solid-state battery, thin-film solid-state battery, rechargeable supercapacitor or the like, and thus may be combined with any type of recharging technology. For example, in some embodiments, the housing may include any of a number of different terminals, electrical connectors or the like to connect to a suitable charger, and in some examples, to connect to other peripherals for communication. More specific suitable examples include direct current (DC) connectors such as cylindrical connectors, cigarette lighter connectors and USB connectors including those specified by USB 1.x (e.g., Type A, Type B), USB 2.0 and its updates and additions (e.g., Mini A, Mini B, Mini AB, Micro A, Micro B, Micro AB) and USB 3.x (e.g., Type A, Type B, Micro B, Micro AB, Type C), proprietary connectors such as Apple's Lightning connector, and the like. The housing may directly connect with the charger or other peripheral, or the two may connect via an appropriate cable that also has suitable connectors. In examples in which the two are connected by cable, the housing and charger or other peripheral may have the same or different type of connector with the cable having the one type of connector or both types of connectors.

In examples involving induction-powered charging, the aerosol delivery device may be equipped with inductive wireless charging technology and include an induction receiver to connect with a wireless charger, charging pad or the like that includes an induction transmitter and uses inductive wireless charging (including for example, wireless charging according to the Qi wireless charging standard from the Wireless Power Consortium (WPC)). Or the power source may be recharged from a wireless radio frequency (RF) based charger. An example of an inductive wireless charging system is described in U.S. Pat. App. Pub. No. 2017/0112196 to Sur et al., which is incorporated herein by reference in its entirety. Further, in some embodiments in the case of an electronic cigarette, the cartridge may comprise a single-use cartridge, as disclosed in U.S. Pat. No. 8,910,639 to Chang et al., which is incorporated herein by reference.

One or more connections may be employed to connect the power source to a recharging technology, and some may involve a charging case, cradle, dock, sleeve or the like. More specifically, for example, the control body may be configured to engage a cradle that includes a USB connector to connect to a power supply. Or in another example, the housing may be configured to fit within and engage a sleeve that includes a USB connector to connect to a power supply. In these and similar examples, the USB connector may connect directly to the power source, or the USB connector may connect to the power source via a suitable power adapter.

It should be noted that one or more control components providing varying functions may be used in the disclosed aerosol delivery devices as will be discussed herein. In some embodiments, the one or more control components may control activation/deactivation of one or both of the first pump and the second pump, and/or control the flow rate exiting one or both of the first pump and the second pump. In the depicted embodiment of FIG. 2, for example, the aerosol delivery device comprises a control component that is configured to control an output flow rate of the first pump and an output flow rate of the second pump. In some embodiments, the control component may further be configured to control the power output from the power source to operate the first and the second pumps. In some embodiments, the power source, the control component, and the first and second liquid pumps are in electrical communication, for example, as depicted by the dashed lines in FIG. 2. In some embodiments, one or more additional components may be included within the housing, such as a flow sensor, flow controllers, additional control components, activation mechanisms, and the like.

In some embodiments, the aerosol delivery device may include multiple control components that individually, or in combination, control the functionality of specific components within the aerosol delivery device as noted above. A suitable control component may include a number of electronic components, and in some examples may be formed of a printed circuit board (PCB). In some examples, the electronic components include processing circuitry configured to perform data processing, application execution, or other processing, control or management services according to one or more example embodiments. The processing circuitry may include a processor embodied in a variety of forms such as at least one processor core, microprocessor, coprocessor, controller, microcontroller or various other computing or processing devices including one or more integrated circuits such as, for example, an ASIC (application specific integrated circuit), an FPGA (field programmable gate array), some combination thereof, or the like. In some examples, the processing circuitry may include memory coupled to or integrated with the processor, and which may store data, computer program instructions executable by the processor, some combination thereof, or the like.

In some example embodiments, the control component may include one or more input/output peripherals, which may be coupled to or integrated with the processing circuitry. More particularly, the control component may include a communication interface to enable wireless communication with one or more networks, computing devices or other appropriately-enabled devices. Examples of suitable communication interfaces are disclosed in U.S. Pat. App. Pub. No. 2016/0261020 to Marion et al., the content of which is incorporated herein by reference. Another example of a suitable communication interface is the CC3200 single chip wireless microcontroller unit (MCU) from Texas Instruments. In some embodiments, for example, the aerosol delivery device may be configured to send information to an electronic device via Near Field Communication (NFC) or Bluetooth technology. Additional examples of suitable manners according to which the aerosol delivery device may be configured to wirelessly communicate are disclosed in U.S. Pat. App. Pub. No. 2016/0007651 to Ampolini et al., and U.S. Pat. App. Pub. No. 2016/0219933 to Henry, Jr. et al., each of which is incorporated herein by reference. For example, the aerosol delivery device also may communicate with a computer or other device acting as an input via wireless communication. In such embodiments, an APP or other computer program may be used in connection with a computer, mobile device, or other computing device to input control instructions to the aerosol delivery device, such control instructions including, for example, the ability to deliver a desired total particulate matter (TPM) provided per puff, vary the duration and/or strength of aerosol produced per puff, amount of nicotine delivered per puff, and/or one or more different puff characteristics. Such puff characteristics may be controllable by a user of the aerosol delivery device, for example, via programmable user settings. In some embodiments, for example, the pressurized flow of air exiting the first pump and/or the pressurized flow of liquid exiting the second pump may be controlled by the control component (based on one or both of exit flow rate and exit pressure) based on the desired puff characteristics to be delivered to a user. In embodiments where the aerosol delivery device is a puff-actuated device, for example, as discussed further herein, the one or both of the pressure value and the flow rate at which air and/or liquid is delivered to the nozzle from the pumps may be controlled based on user puff characteristics, e.g., the pressure value may vary proportionally to the duration and/or strength of puff, such as may be determined by the magnitude of pressure drop when a user draws on the device.

In some embodiments, the aerosol delivery device may comprise an input element 140 to allow a user to control one or more functions of the device (e.g., as described herein above) and or to provide for activation/deactivation of the sleeve. Any component or combination of components may be utilized as the input element for controlling the function of the aerosol delivery device. For example, one or more pushbuttons may be used as described in U.S. Pub. No. 2015/0245658 to Worm et al., which is incorporated herein by reference. Likewise, a touchscreen may be used as described in U.S. patent application Ser. No. 14/643,626, filed Mar. 10, 2015, to Sears et al., which is incorporated herein by reference. As a further example, components adapted for gesture recognition based on specified movements of the temperature regulating sleeve may be used as an input. See U.S. Pub. 2016/0158782 to Henry et al., which is incorporated herein by reference. Various other components are also contemplated, particularly those suitable for use with aerosol delivery devices, and such components may be incorporated into the present disclosure as discussed more fully herein.

In some embodiments, the aerosol delivery device may further comprise a mouthpiece portion 134 within the outer housing 114. For example, in some embodiments the nozzle 106 may be in fluid communication with the mouthpiece portion 134 such that the atomized liquid produced by the nozzle enters the mouthpiece portion. In some embodiments, the nozzle 106 may be positioned proximate to the mouthpiece portion 134 such that the output of atomized liquid from the nozzle is immediately transferred to the mouthpiece portion. For example, the atomized liquid may be whisked, aspirated, sprayed, or otherwise drawn away from the orifice 108 of the nozzle 106 and out an opening 136 in the mouthpiece portion 134 configured for egress of the atomized liquid therefrom. Other configurations of mouthpiece portions are intended to be contemplated based on this disclosure, for example, such that there is an additional chamber or tubular void between the nozzle and the mouthpiece portion, or a section to provide cooling, or further a section to provide additional flavorings. The mouthpiece portion 134 may be configured as a specifically shaped portion of the outer housing 114 and may be permanently attached thereto, in some embodiments. Alternatively, the mouthpiece portion 134 may be a detachable member that is removably and replaceably attachable to the outer housing 114.

As noted above, the reservoir 110 is configured to contain a liquid composition 112. In some embodiments, the liquid composition 112 may be in the form of an aerosol precursor composition. Suitable aerosol precursor compositions may include, but are not limited to, one or more of a polyhydric alcohol, nicotine, tobacco, a tobacco extract, a flavorant, and other active ingredients. Example aerosol forming materials include polyhydric alcohols (e.g., glycerin, propylene glycol, and triethylene glycol) and/or water, and any other materials which yield a visible aerosol, as well as any combinations thereof. Representative types of aerosol forming materials are set forth in U.S. Pat. No. 4,793,365 to Sensabaugh, Jr. et al.; and U.S. Pat. No. 5,101,839 to Jakob et al.; PCT Pat. App. Pub. No. WO 98/57556 to Biggs et al.; and *Chemical and Biological Studies on New Cigarette Prototypes that Heat Instead of Burn Tobacco*, R. J. Reynolds Tobacco Company Monograph (1988); which are incorporated herein by reference in their entirety. Other representative types of aerosol precursor components and formulations are also set forth and characterized in U.S. Pat. No. 7,726,320 to Robinson et al., U.S. Pat. No. 8,881,737 to Collett et al., and U.S. Pat. No. 9,254,002 to Chong et al.; and U.S. Pat. Pub. Nos. 2013/0008457 to Zheng et al.; 2015/0020823 to Lipowicz et al.; and 2015/0020830 to Koller, as well as WO 2014/182736 to Bowen et al, the disclosures of which are incorporated herein by reference in their entireties. Other aerosol precursors that may be employed include the aerosol precursors that have been incorporated in VUSE® products by R. J. Reynolds Vapor Company, the BLU™ products by Fontem Ventures B. V., the MISTIC MENTHOL product by Mistic Ecigs, MARK TEN products by Nu Mark LLC, the JUUL product by Juul Labs, Inc., and VYPE products by British American Tobacco. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN. Embodiments of effervescent materials can be used with the aerosol precursor composition, and are described, by way of example, in U.S. Pat. App. Pub. No. 2012/0055494 to Hunt et al., which is incorporated herein by reference in its entirety. Further, the use of effervescent materials is described, for example, in U.S. Pat. No. 4,639,368 to Niazi et al.; U.S. Pat. No. 5,178,878 to Wehling et al.; U.S. Pat. No. to Wehling et al.; U.S. Pat. No. 6,974,590 to Pather et al.; U.S. Pat. No. 7,381,667 to Bergquist et al.; U.S. Pat. No. 8,424,541 to Crawford et al; U.S. Pat. No. 8,627,828 to Strickland et al.; and U.S. Pat. No. 9,307,787 to Sun et al.; as well as U.S. Pat. App. Pub. No. 2010/0018539 to Brinkley et al. and PCT WO 97/06786 to Johnson et al., all of which are incorporated by reference herein in their entireties. Additional description with respect to embodiments of aerosol precursor compositions, including description of tobacco or components derived from tobacco included therein, is provided in U.S. Pat. App. Pub. Nos. 2018/0020722 and 2018/0020723, each to Davis et al., which are incorporated herein by reference in their entireties.

As noted above, the aerosol precursor composition may additionally or alternatively include other active ingredients including, but not limited to, a nicotine component, botanical ingredients (e.g., lavender, peppermint, chamomile, basil, rosemary, ginger, *cannabis, ginseng*, maca, hemp, *eucalyptus*, rooibos, fennel, citrus, cloves, and tisanes), stimulants (e.g., caffeine and guarana), amino acids (e.g., taurine, theanine, phenylalanine, tyrosine, and tryptophan) and/or pharmaceutical, nutraceutical, medicinal ingredients (e.g., vitamins, such as B6, B12, and C, and/or cannabinoids, such as tetrahydrocannabinol (THC) and cannabidiol (CBD)), and combinations thereof.

In some embodiments, the aerosol precursor composition may include one or more acids such as levulinic acid, succinic acid, lactic acid, pyruvic acid, benzoic acid, fumaric acid, combinations thereof, and the like. Inclusion of an acid(s) in liquid aerosol precursor compositions including nicotine may provide a protonated liquid aerosol precursor composition, including nicotine in salt form. Representative types of liquid aerosol precursor components and formulations are set forth and characterized in U.S. Pat. No. 7,726,320 to Robinson et al., U.S. Pat. No. 9,254,002 to Chong et al., and U.S. Pat. App. Pub. Nos. 2013/0008457 to Zheng et al., 2015/0020823 to Lipowicz et al., and 2015/0020830 to Koller, as well as PCT Pat. App. Pub. No. WO 2014/182736 to Bowen et al., and U.S. Pat. No. 8,881,737 to Collett et al., the disclosures of which are incorporated herein by reference.

As noted above, in some embodiments the aerosol precursor composition comprises a glycerol-based liquid. In other embodiments, however, the aerosol precursor composition may be a water-based liquid. Such water-based liquids may be referred to as "water-based aerosol precursor compositions," "aerosol precursor compositions," and/or "water-based liquids" and generally include any ingredients discussed herein above in reference to aerosol precursor compositions. In some embodiments, the aerosol precursor composition may be comprised of more than approximately 60% water. For example, in some embodiments about 60% or greater water by weight, or about 65% or greater water by weight, or about 70% or greater water by weight, or about 75% or greater water by weight, or about 80% or greater water by weight, or about 85% or greater water by weight, or about 90% or greater water by weight, based on the total weight of the water-based aerosol precursor composition. In some embodiments, the water-based liquid may include up to approximately 10% propylene glycol. For example, in some embodiments the percentage of propylene glycol in the water-based liquid may be in the inclusive range of approximately 4% to approximately 5%. In some embodiments, the water-based liquid may include up to approximately 10% flavorant. For example, in some embodiments the percentage of flavorant(s) of the water-based liquid may be in the inclusive range of approximately 3% to approximately 7%. In some implementations, the water-based liquid may include up to approximately 1% nicotine. For example, in some embodiments the percentage nicotine in the water-based liquid may be in the inclusive range of approximately 0.1% to approximately 0.3%. In some embodiments, the water-based liquid may include up to approximately 10% cyclodextrin. For example, in some embodiments the percentage cyclodextrin in the water-based liquid may be in the inclusive range of approximately 3% to 5%. In still other embodiments, the aerosol precursor composition may be a combination of a glycerol-based liquid and a water-based liquid. For example, some embodiments may include up to approximately 50% water and less than approximately 20% glycerol. The remaining components may include one or more of propylene glycol, flavorants, nicotine, cyclodextrin, etc. Some examples of water-based liquid compositions that may be suitable are disclosed in GB 1817863.2, filed Nov. 1, 2018, titled *Aerosolisable Formulation*; GB 1817864.0, filed Nov. 1, 2018, titled *Aerosolisable Formulation*; GB 1817867.3, filed Nov. 1, 2018, titled *Aerosolisable Formulation*; GB 1817865.7, filed Nov. 1, 2018, titled *Aerosolisable Formulation*; GB 1817859.0, filed Nov. 1, 2018, titled *Aerosolisable Formulation*; GB 1817866.5, filed Nov. 1, 2018, titled *Aerosolisable Formulation*; GB 1817861.6, filed Nov. 1, 2018, titled *Gel and Crystalline Powder*; GB 1817862.4, filed Nov. 1, 2018, titled *Aerosolisable Formulation*; GB 1817868.1, filed Nov. 1, 2018, titled *Aerosolised Formulation*; and GB 1817860.8, filed Nov. 1, 2018, titled *Aerosolised Formulation*, each of which is incorporated by reference herein in its entirety.

As noted above, in various embodiments the liquid composition 112 may also include a flavorant. In some embodiments, the flavorant may be pre-mixed with the liquid. In other embodiments, the flavorant may be delivered separately downstream from the nozzle as a main or secondary flavor. Still other embodiments may combine a pre-mixed flavorant with a downstream flavorant. As used herein, reference to a "flavorant" refers to compounds or components that can be aerosolized and delivered to a user and which impart a sensory experience in terms of taste and/or aroma. Example flavorants include, but are not limited to, vanillin, ethyl vanillin, cream, tea, coffee, fruit (e.g., apple, cherry, strawberry, peach and citrus flavors, including lime, lemon, mango, and other citrus flavors), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, amaretto, mojito, yerba santa, *ginseng*, chamomile, turmeric, bacopa monniera, gingko *biloba*, withania somnifera, cinnamon, sandalwood, jasmine, cascarilla, cocoa, licorice, terpenes, trigeminal sensates and flavorings and flavor packages of the type and character traditionally used for the flavoring of cigarette, cigar, and pipe tobaccos. Other examples include flavorants derived from, or simulating, burley, oriental tobacco, flue cured tobacco, etc. Syrups, such as high fructose corn syrup, also can be employed. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components are variable based upon factors such as the sensory characteristics that are desired for the smoking article, and the present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be noted that reference to a flavorant should not be limited to any single flavorant as described above, and may, in fact, represent a combination of one or more flavorants.

Figure 3:
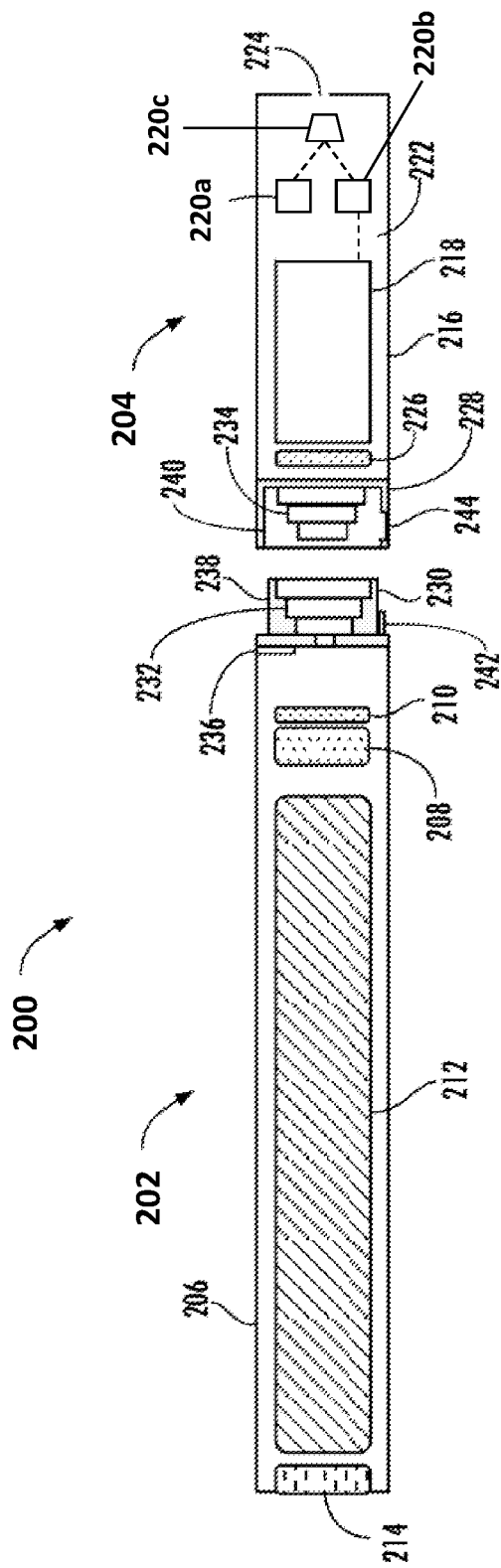
Figure 4:
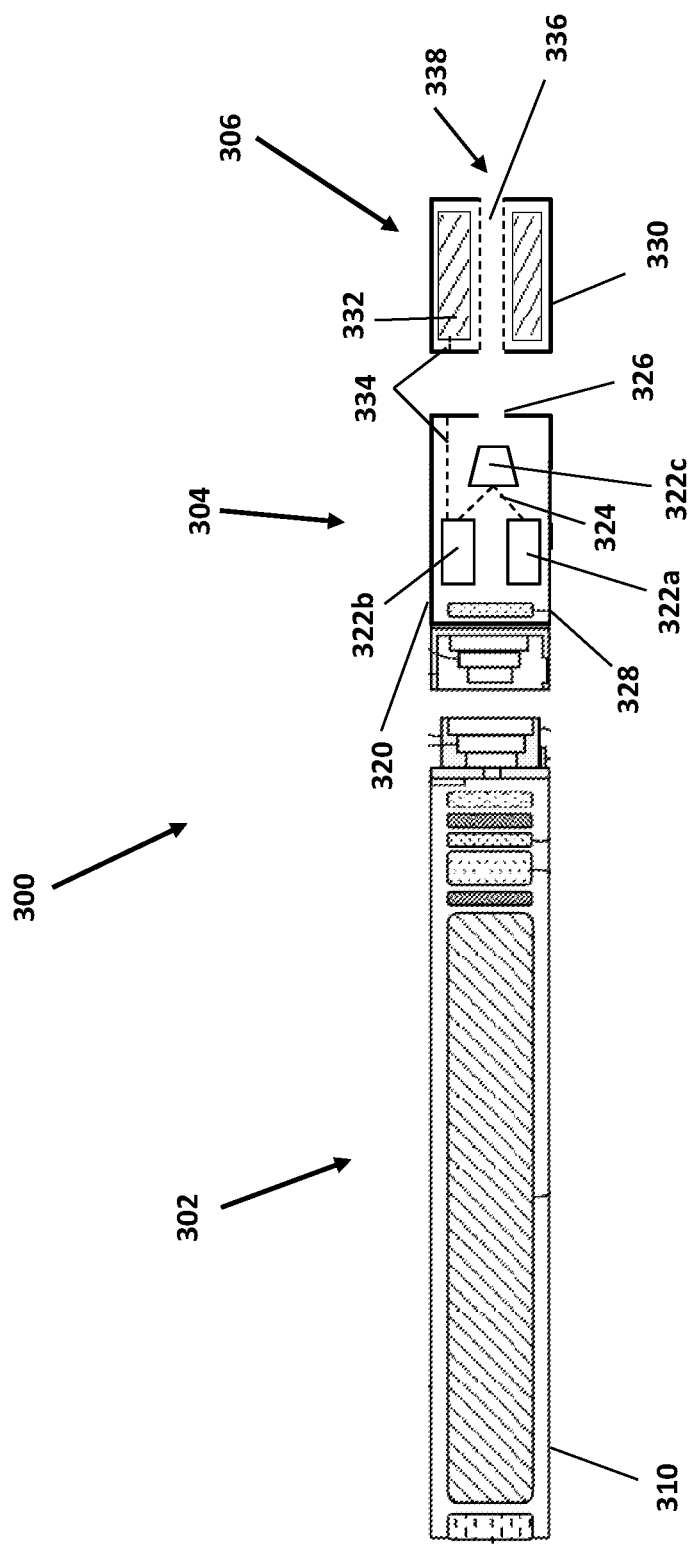
FIG. 4 illustrates a front cross-section schematic view of an example aerosol delivery device having a three-piece design including a control body, an atomizing section, and a reservoir housing, wherein the control body, the atomizing section, and the reservoir housing are shown in a de-coupled configuration, according to an example embodiment of the present disclosure.

As noted above, in some embodiments the aerosol delivery device may have a multi-piece design, such as a two-piece design (e.g., as depicted in FIG. 3) or a three-piece design (e.g., as depicted in FIG. 4). In such embodiments, the reservoir may be positioned within a distinct section of the device (e.g., the control body or the cartridge portion as depicted in FIG. 3), or such that the reservoir is substantially self-contained within a separate reservoir housing that is removably coupleable to one or more other sections of the aerosol delivery device, as depicted in FIG. 4).

FIG. 3 illustrates an embodiment of an aerosol delivery device having a two-piece design including a control body and a cartridge in the case of an aerosol delivery device. In this regard, FIG. 3 illustrates an aerosol delivery device 200 according to an example embodiment of the present disclosure having a two-piece design, for example. As indicated, the aerosol delivery device may include a control body 202 and a cartridge 204. The control body and the cartridge can be permanently or detachably aligned in a functioning relationship. In this regard, an aerosol delivery device may be provided in a coupled configuration (not shown), whereas FIG. 3 illustrates a partially cut-away side view of the aerosol delivery device in a decoupled configuration. The aerosol delivery device may, for example, be substantially rod-like, substantially tubular shaped, or substantially cylindrically shaped in some implementations when the control body and the cartridge are in an assembled configuration. However various other configurations are intended to be contemplated in the present disclosure, for example, configurations with a substantially modular or pod-like shape (e.g., the control body 202 may be configured to have a receiving chamber into which a portion of the cartridge 204 may be received to form a working connection).

As depicted in FIG. 3, the control body 202 and the cartridge 204 can be configured to engage one another by a variety of connections, such as a press fit (or interference fit) connection, a threaded connection, a magnetic connection, or the like. As such, the control body may include a first engaging element (e.g., a coupler) that is adapted to engage a second engaging element (e.g., a connector) on the cartridge. The first engaging element and the second engaging element may be reversible. As an example, either of the first engaging element or the second engaging element may be a male thread, and the other may be a female thread. As a further example, either the first engaging element or the second engaging element may be a magnet, and the other may be a metal or a matching magnet. In particular implementations, engaging elements may be defined directly by existing components of the control body and the cartridge. For example, the housing of the control body may define a cavity at an end thereof that is configured to receive at least a portion of the cartridge (e.g., a storage tank or other shell-forming element of the cartridge). In particular, a storage tank of the cartridge may be at least partially received within the cavity of the control body while a mouthpiece of the cartridge remains exposed outside of the cavity of the control body. The cartridge may be retained within the cavity formed by the control body housing, such as by an interference fit (e.g., through use of detents and/or other features creating an interference engagement between an outer surface of the cartridge and an interior surface of a wall forming the control body cavity), by a magnetic engagement (e.g., though use of magnets and/or magnetic metals positioned within the cavity of the control body and positioned on the cartridge), or by other suitable techniques.

As seen in the cut-away view illustrated in FIG. 3, the control body 202 and cartridge 204 may each include a number of respective components. The components illustrated in FIG. 3 are representative of the components that may be present in a control body and cartridge and are not intended to limit the scope of components that are encompassed by the present disclosure or to require the use of any specific components in various embodiments as described herein. As shown, for example, the control body can be formed of a housing 206 (sometimes referred to as a control body shell) that can include a control component 208 (e.g., processing circuitry, etc.), a flow sensor 210, a power source 212 (e.g., battery, supercapacitor), and an indicator 214 (e.g., LED, quantum dot-based LED), and such components can be variably aligned. The power source may be rechargeable, and the control component may include a switch and processing circuitry coupled to the flow sensor and the switch. The processing circuitry may be configured to determine a difference between measurements of atmospheric air pressure from the flow sensor, and a reference atmospheric air pressure. In some implementations, the flow sensor is an absolute pressure sensor.

As noted above, in some embodiments the aerosol delivery device may comprise a power source, such as a battery, that is positioned within the housing of the control body. Any suitable power source as described herein above with respect to FIG. 2 may be suitable for use in such embodiments. In some embodiments, the power source may also comprise a capacitor. Capacitors are capable of discharging more quickly than batteries and can be charged between puffs, allowing the battery to discharge into the capacitor at a lower rate than if it were used to power the two or more separate components at one time. For example, a supercapacitor—e.g., an electric double-layer capacitor (EDLC)—may be used separate from or in combination with a battery. When used alone, the supercapacitor may be recharged before each use of the article. Thus, the device may also include a charger component that can be attached to the smoking article between uses to replenish the supercapacitor.

Further components may be utilized in the aerosol delivery device of the present disclosure. For example, the aerosol delivery device may include a flow sensor that is sensitive either to pressure changes or air flow changes as the consumer draws on the article (e.g., a puff-actuated switch). Other possible current actuation/deactuation mechanisms may include a temperature actuated on/off switch or a lip pressure actuated switch. An example mechanism that can provide such puff-actuation capability includes a Model 163PC01D36 silicon sensor, manufactured by the MicroSwitch division of Honeywell, Inc., Freeport, Ill. Representative flow sensors, current regulating components, and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference is also made to the control schemes described in U.S. Pat. No. 9,423,152 to Ampolini et al., which is incorporated herein by reference in its entirety.

In another example, an aerosol delivery device may comprise a first conductive surface configured to contact a first body part of a user holding the device, and a second conductive surface, conductively isolated from the first conductive surface, configured to contact a second body part of the user. As such, when the aerosol delivery device detects a change in conductivity between the first conductive surface and the second conductive surface, a vaporizer is activated to vaporize a substance so that the vapors may be inhaled by the user holding unit. The first body part and the second body part may be a lip or parts of a hand(s). The two conductive surfaces may also be used to charge a battery contained in the personal vaporizer unit. The two conductive surfaces may also form, or be part of, a connector that may be used to output data stored in a memory. Reference is made to U.S. Pat. No. 9,861,773 to Terry et al., which is incorporated herein by reference in its entirety.

Yet other components are also contemplated, particularly those suitable for use with aerosol delivery devices may be incorporated into the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and PCT Pat. App. Pub. No. WO 2010/003480 by Flick discloses a fluid flow sensing system indicative of a puff in an aerosol generating system; all of the foregoing disclosures being incorporated herein by reference.

Further examples of components related to electronic aerosol delivery articles and disclosing materials or components that may be used in the present device include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; PCT Pat. App. Pub. No. WO 2010/091593 to Hon; and PCT Pat. App. Pub. No. WO 2013/089551 to Foo, each of which is incorporated herein by reference in its entirety. Further, U.S. Pat. App. Pub. No. 2017/0099877 to Worm et al., filed Oct. 13, 2015, discloses capsules that may be included in aerosol delivery devices and fob-shape configurations for aerosol delivery devices, and is incorporated herein by reference in its entirety. A variety of the materials disclosed by the foregoing documents may be incorporated into the present devices in various embodiments, and all of the foregoing disclosures are incorporated herein by reference in their entireties.

As noted in FIG. 3, in this depicted embodiment the cartridge 204 can be formed of a housing 216 (sometimes referred to as the cartridge shell) enclosing a reservoir 218 configured to retain a liquid composition, and including a first pump 220a, a second pump 220b, and a nozzle 220c. Examples of suitable reservoir, pumps, and nozzles for use in the depicted embodiment are described herein above with respect to the embodiments depicted in FIGS. 2. 1 and 2. However, as depicted in FIG. 3, the reservoir 218 may be permanently positioned within the housing 216 of the cartridge portion 204. In such embodiments, the reservoir may be configured such that it is refillable by a user of the aerosol delivery device without being physically removed from the housing. Optionally, some embodiments may provide for an aerosol delivery device that is disposable or wherein a portion (e.g., such as the cartridge portion) of the aerosol delivery device is disposable and/or replaceable.

As shown, in the depicted embodiment, the reservoir, the first pump, the second pump, and/or the nozzle may be interconnected either directly or indirectly as depicted by the dashed lines 222 and as described herein above with respect to FIGS. 1 and 2. Further, in some embodiments, a mouthpiece portion 224 having an opening may be present in the housing 216 (e.g., at the mouth end of the cartridge) to allow for egress of the atomized liquid from the mouthpiece portion 224. The cartridge 204 also may include one or more flow controlling components 226, which may include an integrated circuit, a control component, a flow sensor, or the like. The one or more flow controlling components may be adapted to communicate with one or more of the control component 208, the flow sensor 210, the power source 212, the first pump 220a, and the second pump 220b. The one or more flow controlling components may be positioned anywhere within the cartridge or a base 228 thereof. The one or more flow controlling components, as noted above, may be configured to control the output flow rate from the first pump 220a and the second pump 220b. Any suitable control component capable of controlling the flow rate and/or the pressure output of the pressurized flow of air or the pressurized flow of liquid exiting the pumps, such as any of those mentioned herein above, may be suitable for use in aerosol delivery devices according to the present disclosure.

The control body 202 and the cartridge 204 may include components adapted to facilitate a fluid engagement therebetween. As illustrated in FIG. 3, the control body can include a coupler 230 having a cavity 232 therein. The base 228 of the cartridge can be adapted to engage the coupler and can include a projection 234 adapted to fit within the cavity. Such engagement can facilitate a stable connection between the control body and the cartridge as well as establish an electrical connection between the power source 212 and control component 208 in the control body and the one or more flow controlling components 226 and the first pump 220a and the second pump 220b in the cartridge. Further, the housing 206 can include an air intake 236, which may be a notch in the housing where it connects to the coupler that allows for passage of ambient air around the coupler and into the housing where it then passes through the cavity 232 of the coupler and into the cartridge through the projection 234. For example, when a user draws upon the mouth end of the aerosol delivery device or when the first pump 220a is engaged to force air into the aerosol delivery device, this suction force causes ambient air to enter the air intake 236 and pass through the cavity 232 in the coupler 230 and the central opening in the projection 234 of the base 228. In the nozzle 220c, the drawn air combines with a liquid composition to form an atomized liquid. The atomized liquid is whisked, aspirated, sprayed, or otherwise drawn away from the nozzle 220c and out the opening in the mouthpiece portion 224 of the aerosol delivery device.

A coupler and a base useful according to the present disclosure are described in U.S. Pat. App. Pub. No. 2014/0261495 to Novak et al., which is incorporated herein by reference. For example, the coupler 230 as seen in FIG. 3 may define an outer periphery 238 configured to mate with an inner periphery 240 of the base 228. In one example the inner periphery of the base may define a radius that is substantially equal to, or slightly greater than, a radius of the outer periphery of the coupler. Further, the coupler may define one or more protrusions 242 at the outer periphery configured to engage one or more recesses 244 defined at the inner periphery of the base. However, various other examples of structures, shapes and components may be employed to couple the base to the coupler. In some examples the connection between the base of the cartridge 204 and the coupler of the control body 202 may be substantially permanent, whereas in other examples the connection therebetween may be releasable such that, for example, the control body may be reused with one or more additional cartridges that may be disposable and/or refillable. For further detail regarding embodiments of an aerosol delivery device including a control body and a cartridge in the case of an electronic cigarette, see the above-cited U.S. patent application Ser. No. 15/836,086 to Sur; and U.S. patent application Ser. No. 15/916,834 to Sur et al.; as well as U.S. patent application Ser. No. 15/916,696 to Sur, filed Mar. 9, 2018, which is also incorporated herein by reference.

Figure 5:
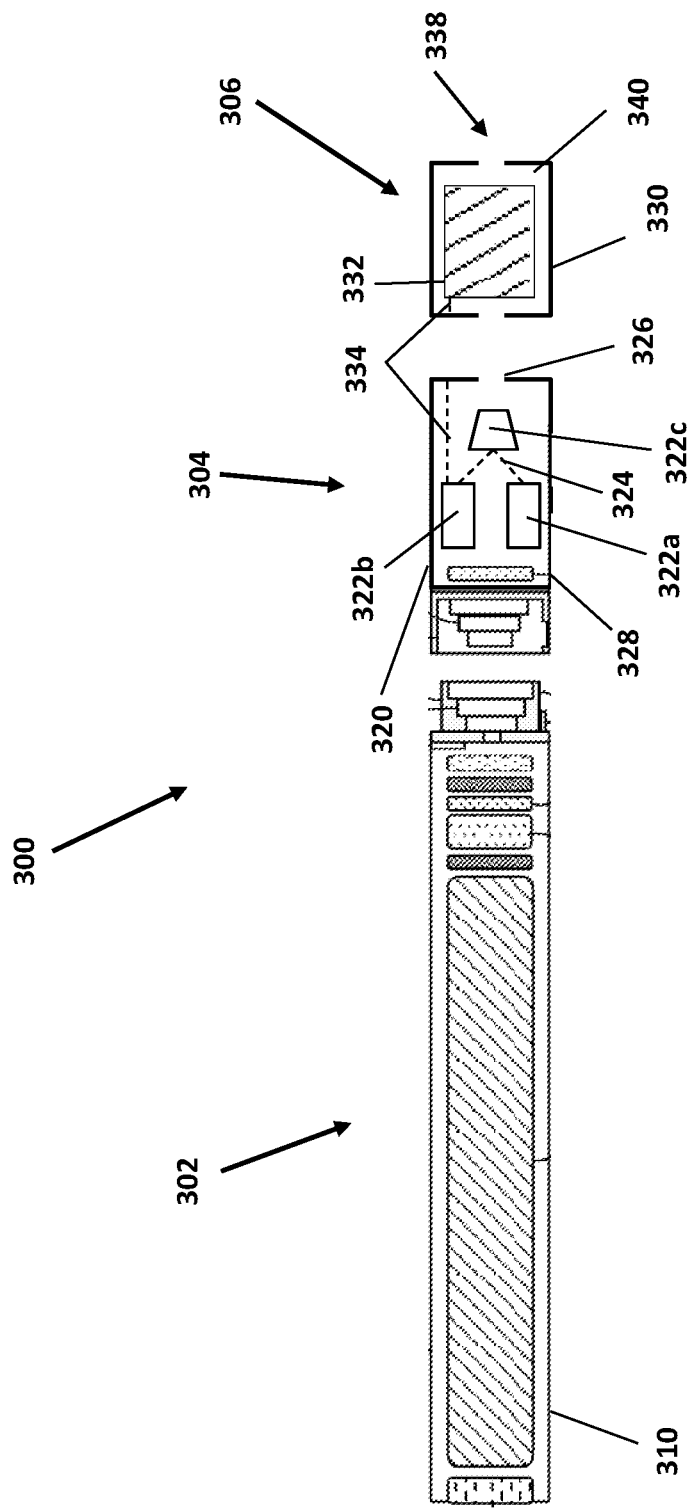
FIG. 5 illustrates a front cross-section schematic view of an example aerosol delivery device having a three-piece design including a control body, an atomizing section, and a reservoir housing, wherein the control body, the atomizing section, and the reservoir housing are shown in a de-coupled configuration, according to an example embodiment of the present disclosure

FIGS. 4 and 5 illustrate an aerosol delivery device having a three-piece design, according to an example embodiment of the present disclosure having a three-piece design. As indicated, the aerosol delivery device 300 may include a control body 302, an atomizing section 304, and a reservoir section 306. The control body, the atomizing section, and the reservoir section can be permanently or detachably aligned in a functioning relationship, for example, as described above with respect to the attachment of the control body and the cartridge in FIG. 3. For example, the control body, the atomizing section, and the reservoir sections may engage one another by a variety of connections, such as a press fit (or interference fit) connection, a threaded connection, a magnetic connection, or the like. In some embodiments, the control body may include a first engaging element (e.g., a coupler) that is adapted to engage a second engaging element (e.g., a connector) on the atomizing housing, and the atomizing housing may include a third engaging element (e.g., a coupler) that is adapted to engage a fourth engaging element (e.g., a connector) on the reservoir housing. The engagement mechanism between, and/or the configuration and arrangement of, the control body, the atomizing section, and the reservoir section may vary. Generally, the control body 302 and the atomizing section 304 may each include a number of respective components therein. In some embodiments, the control body 302 may include a housing 310 which can include any number of components illustrated in the control body of FIG. 3, for example, a control component (e.g., processing circuitry, etc.), a flow sensor, a power source (e.g., battery, supercapacitor), and an indicator (e.g., LED, quantum dot-based LED), and such components can be variably aligned.

As noted in FIGS. 4 and 5, in the depicted embodiments the atomizing section 304 can be formed of a housing 320 (sometimes referred to as the atomizer housing) enclosing a first pump 322a, a second pump 322b, and a nozzle 322c. Examples of suitable pumps and nozzles for use in the depicted embodiments are described herein above with respect to the embodiments depicted in FIGS. 1 and 2. As shown in FIGS. 4 and 5, in some embodiments, the first pump, the second pump, and/or the nozzle may be interconnected either directly or indirectly as depicted by the dashed lines 324 and as described herein above with respect to FIGS. 1 and 2. Further, in some embodiments, an opening 326 may be present in the atomizer housing 320 (e.g., proximate to the reservoir section 306) to allow for egress of the atomized liquid from the atomizer section 304 to the reservoir section 306, when variably aligned. In other embodiments, a valve, gate, or other mechanical component may be used in place of the opening 326 so as to allow for egress of the atomized liquid from the atomizing section 304 to the reservoir section 306, when variably aligned and coupled together. Other configurations, however, may be possible.

Generally, it should be noted that any of the representative components, arrangements, features, and/or configurations mentioned herein above with reference to the aerosol delivery device of FIG. 3 may, likewise, be incorporated in various capacities into the aerosol delivery devices as illustrated in FIGS. 4 and 5. For example, the atomizing section 304 also may include one or more flow controlling components 328 which may include an integrated circuit, a control component, a flow sensor, or the like. In some embodiments, the one or more flow controlling 328 components may be adapted to communicate with a control component, for example, in the control body 302. For example, the one or more flow controlling components, as noted above, may be configured to control the output flow rate from the first pump 322a and the second pump 322b. Any suitable control component capable of controlling the flow rate and/or the pressure output of the pressurized flow of air or the pressurized flow of liquid exiting the pumps, such as any of those mentioned herein above, may be suitable for use in aerosol delivery devices according to the present disclosure.

In some embodiments, the reservoir section 306 may be formed of a reservoir housing 330, which includes a reservoir 332 contained therein. The embodiments depicted in FIGS. 4 and 5, for example, provide a configuration wherein a reservoir 332 is completely self-contained within a separate portion of the aerosol delivery device, e.g., in the reservoir housing 330. Advantageously, the depicted embodiment allows for the control body 302 and the atomizing section 304, and the components thereof, to be reusable by a user of the aerosol delivery device. For example, as depicted in FIGS. 4 and 5, the reservoir housing 306 may be removably coupleable to the atomizing section, such that the reservoir housing can be easily removed and replaced. Other configurations, however, may be possible. In some embodiments, the reservoir housing may also be entirely reusable, for example, the reservoir housing may be removed, refilled by a user of the device, and then reused. Generally, the reservoir 332 may be interconnected with the second pump 322b either directly or indirectly when the atomizing section 304 and the reservoir section 306 are coupled together, e.g., as depicted by the dashed lines 334 and as described herein above with respect to FIGS. 1 and 2.

As depicted in FIG. 4, in some embodiments the reservoir section 306 includes a channel 336 configured for the passage of an aerosol therethrough. In such embodiments, the channel 336 may be variably aligned with the opening 326 in the atomizer housing 320. In the depicted embodiment in FIG. 4, the reservoir section includes an opening 338 in the reservoir housing 330 configured for egress of an aerosol therethrough. In some embodiments, the opening 338 may be variably aligned with the channel 336 and/or the opening 326 in the atomizer housing 320. In other embodiments, the channel may not be present, for example, as depicted in FIG. 5, there may be one or more voids 340 (e.g., a cavity or open space allowing for air flow and/or aerosol passage therethrough) between the reservoir 332 and the reservoir housing 330 within the reservoir section configured to allow for flow of the aerosol around the reservoir 332 positioned therein. Such configurations allow for the flow of an aerosol generated in the atomizing section 304 through the reservoir section 306 and to a user of the aerosol delivery device via the opening 338 in the reservoir housing 330.

Many modifications and other implementations of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device configured to deliver a pressurized flow of air and a pressurized flow of liquid, the aerosol delivery device comprising:
   a reservoir configured to contain a liquid; and
   a nozzle comprising an orifice, the nozzle being configured to receive the pressurized flow of air and the pressurized flow of liquid and the orifice being adapted to spray the liquid in an atomized form,
   wherein the liquid is an aerosol precursor composition that is water-based so as to comprise about 60% or greater water by weight, based on the total weight of the aerosol precursor composition,
   wherein the pressurized flow of air and the pressurized flow of liquid are separately transferred to the orifice without mixing within the nozzle.

2. The aerosol delivery device of claim 1, wherein the nozzle is positioned proximate to a mouthpiece portion.

3. The aerosol delivery device of claim 2, wherein the mouthpiece portion is configured to receive a flow of the atomized liquid from the nozzle and has an opening for egress of the atomized liquid from the mouthpiece portion.

4. The aerosol delivery device of claim 1, wherein the reservoir is in fluid communication with the nozzle.

5. The aerosol delivery device of claim 1, wherein the reservoir is removable and replaceable by a user of the aerosol delivery device.

6. The aerosol delivery device of claim 1, wherein the reservoir is refillable by a user of the aerosol delivery device.

7. The aerosol delivery device of claim 1, wherein the aerosol precursor composition comprises one or more of a polyhydric alcohol, tobacco, a tobacco extract, a flavorant, a nicotine component, botanicals, nutraceuticals, stimulants, amino acids, vitamins, cannabinoids, and combinations thereof.

8. The aerosol delivery device of claim 1, further comprising:
   a first pump configured to deliver the pressurized flow of air to the nozzle; and
   a second pump configured to deliver the pressurized flow of liquid to the nozzle.

9. The aerosol delivery device of claim 8, wherein the first pump is configured to deliver the pressurized flow of air to the nozzle at a flow rate in the range of about 1 L/min to about 10 L/min and a pressure in the range of about 0.1 psi to about 10 psi.

10. The aerosol delivery device of claim 8, wherein the second pump is configured to deliver the pressurized flow of liquid to the nozzle at a flow rate in the range of about 0.1 mL/min to about 10 mL/min and a pressure in the range of about 0.1 psi to about 10 psi.

11. The aerosol delivery device of claim 8, further comprising a power source and a control component.

12. The aerosol delivery device of claim 11, wherein the control component is configured to control one or both of an output flow rate of the first pump and an output flow rate of the second pump.

13. The aerosol delivery device of claim 11, wherein the control component is configured to control power output from the power source to one or both of the first pump and the second pump, and wherein the power source is configured to provide sufficient power to operate both the first pump and the second pump simultaneously.

14. The aerosol delivery device of claim 1, further comprising a housing and at least one opening in the housing for receiving air.

15. An aerosol delivery device configured to deliver a pressurized flow of air and a pressurized flow of liquid, the aerosol delivery device comprising:
   a reservoir configured to contain a liquid; and
   a nozzle comprising an orifice, the nozzle being configured to receive the pressurized flow of air and the pressurized flow of liquid and the orifice being adapted to spray the liquid in an atomized form, wherein a fluid pressure within the nozzle is in the range of about 0.1 psi to about 10 psi,
   wherein the pressurized flow of air and the pressurized flow of liquid are separately transferred to the orifice without mixing within the nozzle.

* * * * *